(12) United States Patent
Franganillo et al.

(10) Patent No.: US 9,283,844 B2
(45) Date of Patent: Mar. 15, 2016

(54) VEHICLE SPEED CONTROL SYSTEM AND METHOD

(71) Applicant: Jaguar Land Rover Limited, Whitley, Coventry, Warwickshire (GB)

(72) Inventors: Diana Franganillo, Leamington Spa (GB); Simon Gilling, Kenilworth (GB); Andrew Fairgrieve, Rugby (GB); Daniel Woolliscroft, Birmingham (GB); James Kelly, Solihull (GB)

(73) Assignee: Jaguar Land Rover Limited, Whitley, Coventry, Warwickshire (GB)

( * ) Notice: Subject to any disclaimer, the term of this patent is extended or adjusted under 35 U.S.C. 154(b) by 0 days.

(21) Appl. No.: 14/214,735

(22) Filed: Mar. 15, 2014

(65) Prior Publication Data

US 2014/0277988 A1 Sep. 18, 2014

(30) Foreign Application Priority Data

Mar. 15, 2013 (GB) .................................. 1304707.1

(51) Int. Cl.
G05D 13/00 (2006.01)
B60K 23/00 (2006.01)
G01N 7/14 (2006.01)

(52) U.S. Cl.
CPC . *B60K 23/00* (2013.01); *G01N 7/14* (2013.01)

(58) Field of Classification Search
USPC ............ 701/1, 36, 70, 71, 74, 76, 81, 82, 83, 701/93, 94, 97; 340/425.5, 438, 439; 180/170, 171, 178, 179, 197, 271, 272
See application file for complete search history.

(56) References Cited

U.S. PATENT DOCUMENTS

| | | | | |
|---|---|---|---|---|
| 4,989,149 A | * | 1/1991 | Mimura et al. | 701/95 |
| 5,713,428 A | * | 2/1998 | Linden et al. | 180/179 |
| 6,324,463 B1 | * | 11/2001 | Patel | 701/93 |
| 6,374,173 B1 | * | 4/2002 | Ehlbeck | 701/93 |
| 6,637,534 B2 | | 10/2003 | Barbehoen et al. | |
| 2002/0133285 A1 | * | 9/2002 | Hirasago | 701/96 |

(Continued)

FOREIGN PATENT DOCUMENTS

| | | |
|---|---|---|
| DE | 4437678 A1 | 5/1996 |
| DE | 10041745 A1 | 3/2002 |
| DE | 10145915 A1 | 4/2003 |

(Continued)

OTHER PUBLICATIONS

Written Opinion & International Search Report for PCT/EP2014/050775 dated Apr. 29, 2014, 16 pages.

*Primary Examiner* — Thomas Tarcza
*Assistant Examiner* — Edward Pipala
(74) *Attorney, Agent, or Firm* — Reising Ethington P.C.

(57) ABSTRACT

A system for controlling vehicle speed in accordance with a current value of vehicle set-speed. The system responds to user input to change the current value of vehicle set-speed to a different value and is configured to store the current value of set-speed in a memory as a stored set-speed and to change the current value of set-speed in dependence on the user input. The speedometer indicates both the current and stored set-speeds. The system can return the current value of vehicle set-speed to the stored set-speed upon receipt of a "resume" or other user command. The system can enter into a descent control mode that applies braking torque but no drive torque and can also enter into a full functionality mode that provides either drive or braking torque to maintain the vehicle at the set-speed.

20 Claims, 9 Drawing Sheets

(56) References Cited

U.S. PATENT DOCUMENTS

2004/0084237 A1* 5/2004 Petrie, Jr. .................. 180/170
2009/0322505 A1* 12/2009 Sullivan et al. ............. 340/438

FOREIGN PATENT DOCUMENTS

| DE | 102010028486 A1 | 11/2011 |
| EP | 1657104 A1 | 5/2006 |

* cited by examiner

VEHICLE SPEED CONTROL SYSTEM AND METHOD

FIELD OF THE INVENTION

The invention relates to a system for controlling the speed of a vehicle. In particular, but not exclusively, the invention relates to a system for controlling the speed of a land-based vehicle which is capable of driving in a variety of different and extreme terrains and conditions.

BACKGROUND TO THE INVENTION

In known vehicle speed control systems, typically referred to as cruise control systems, the vehicle speed is maintained on-road once set by the user without further intervention by the user so as to improve the driving experience for the user by reducing workload.

The user selects a speed at which the vehicle is to be maintained, and the vehicle is maintained at that speed for as long as the user does not apply a brake or, in some systems, the clutch. The cruise control system takes its speed signal from the driveshaft or wheel speed sensors. When the brake or the clutch is depressed, the cruise control system is disabled so that the user can override the cruise control system and change the vehicle speed without resistance from the system. If the user depresses the accelerator pedal the vehicle speed will increase, but once the user removes his foot from the accelerator pedal the vehicle reverts to the pre-set cruise speed.

More sophisticated cruise control systems are integrated into the engine management system and may include an adaptive functionality which takes into account the distance to the vehicle in front using a radar-based system. For example, the vehicle may be provided with a forward-looking radar detection system so that the speed and distance of the vehicle in front is detected and a safe following speed and distance is maintained automatically without the need for user input. If the lead vehicle slows down, or another object is detected by the radar detection system, the system sends a signal to the engine or the braking system to slow the vehicle down accordingly, to maintain a safe following distance.

Such systems are usually operable only above a certain speed, typically around 15-20 mph, and are ideal in circumstances in which the vehicle is travelling in steady traffic conditions, and particularly on highways or motorways. In congested traffic conditions, however, where vehicle speed tends to vary widely, cruise control systems are ineffective, and especially where the systems are inoperable because of a minimum speed requirement. A minimum speed requirement is often imposed on cruise control systems so as to reduce the likelihood of low speed collision, for example when parking. Such systems are therefore ineffective in certain driving conditions (e.g. low speed) and are set to be automatically disabled in circumstances in which a user may not consider it to be desirable to do so.

Known cruise control systems also cancel in the event that a wheel slip event is detected requiring intervention by a traction control system (TCS) or stability control system (SCS). Accordingly, they are not well suited to maintaining vehicle progress when driving in off road conditions where such events may be relatively common.

It is also known to provide a control system for a motor vehicle for controlling one or more vehicle subsystems. U.S. Pat. No. 7,349,776, the content of which is hereby incorporated by reference, discloses a vehicle control system comprising a plurality of subsystem controllers including an engine management system, a transmission controller, a steering controller, a brakes controller and a suspension controller. The subsystem controllers are each operable in a plurality of subsystem function modes. The subsystem controllers are connected to a vehicle mode controller which controls the subsystem controllers to assume a required function mode so as to provide a number of driving modes for the vehicle. Each of the driving modes corresponds to a particular driving condition or set of driving conditions, and in each mode each of the sub-systems is set to the function mode most appropriate to those conditions. Such conditions are linked to types of terrain over which the vehicle may be driven such as grass/gravel/snow, mud and ruts, rock crawl, sand and a highway mode known as 'special programs off' (SPO). The vehicle mode controller may be referred to as a Terrain Response® (TR) System or controller.

It is desirable to provide a speed control system capable of controlling vehicle speed at relatively low speeds and whilst driving in off road conditions.

SUMMARY

Embodiments of the invention may be understood with reference to the appended claims.

Aspects of the present invention provide a system, a vehicle and a method.

In one aspect of the invention for which protection is sought there is provided a system for controlling the speed of a vehicle, the system being operable to cause the vehicle to operate in accordance with a current value of vehicle set-speed, the system being operable to allow a user to input a command to change the current value of vehicle set-speed from the current value to a value different from the current value via user input means, upon receipt of the command to change the value of set-speed the system being configured to store the current value of set-speed in a memory as a stored set-speed and to change the current value of set-speed in dependence on the user input, the system being further operable to set the current value of vehicle set-speed to the stored set-speed upon receipt of a user command.

Reference to controlling the vehicle to operate in accordance with a current value of set-speed is to be understood to mean that the system attempts to maintain vehicle speed at the set-speed. In some embodiments, the vehicle attempts to maintain vehicle speed at the set-speed only if one or more conditions are met. For example, the system may set a ceiling on the allowable value of set-speed in dependence on one or more operating conditions, such as a type of terrain over which the vehicle 100 is travelling.

The system may be operable to allow a user to change the current value of set-speed in discrete amounts via the user input means.

The discrete amounts may be input by a user by actuating a control once for each discrete amount by which the user wishes to change the set-speed. In some embodiments, alternatively or in addition the user may change set-speed by a plurality of increments by a single actuation of the control, optionally by holding the control in an actuated condition, for example by holding a button in a depressed condition.

Advantageously the system may be operable to provide a visual indication of the current value of set-speed and a visual indication of the value of stored set-speed.

The system may be operable to provide the visual indication in the form of a current set-speed marker or chaplet and a stored set-speed marker or chaplet at respective locations of a speedometer corresponding to the values of current and stored set-speed.

The system may be operable to set the current value of vehicle set-speed to the stored set-speed upon receipt of a user command only if the user command is received within a prescribed time period of the change of set-speed.

The system may be operable to provide the visual indication of the stored-set-speed only for the duration of the prescribed time period.

Advantageously the system may be operable to allow a user to command a reduction in the current value of vehicle set-speed by either one of first and second input devices, the system being operable to store the current value of set-speed in a memory as a stored set-speed and subsequently to set the current value of vehicle set-speed to the stored set-speed upon receipt of a user command only if the reduction in set-speed is commanded by the second input device.

The second input device may be a user operable brake control.

The first input device may be a user operable control button.

In a further aspect of the invention for which protection is sought there is provided a vehicle comprising the system described in the preceeding paragraphs.

In a still further aspect of the invention for which protection is sought there is provided a method of controlling the speed of a vehicle, comprising: causing a vehicle to operate in accordance with a current value of vehicle set-speed; receiving a user command to change the current value of vehicle set-speed from the current value to a value different from the current value via user input means; upon receipt of the command to change the value of set-speed, storing the current value of set-speed in a memory as a stored set-speed and changing the current value of set-speed in dependence on the user input, the method further comprising setting the current value of vehicle set-speed to the stored set-speed upon receipt of a user command.

In one aspect of the invention for which protection is sought there is provided a system for controlling the speed of a vehicle, the system being configured to control the vehicle according to a first set-speed, the system being operable to allow a user to command the vehicle to operate at a second set-speed that is lower than the first set-speed via user input means, the second set speed being determined by the system in dependence on the value of the first set speed, the system being operable to store the value of the first set-speed in a memory, the system being operable to receive a command from the user to resume operation at the first set-speed stored in the memory, the system being operable to resume operation at the first set-speed stored in the memory upon receipt of the command.

The system may be operable to allow the user to input the first set-speed via the user input means.

The system may be operable to decrease the value of the second set-speed in prescribed decrements in response to user input via the user input means, wherein the second set-speed is a speed that is lower than the first set-speed by an amount selected in dependence on the user command.

The system may be operable to receive a user command to decrease set-speed from either one of first and second user input controls.

The system may be operable to resume operation at the first set-speed only if the user employed the second of the first and second user input controls to reduce the set-speed from the first set-speed to the second set-speed.

In an aspect of the invention for which protection is sought there is provided a system for controlling the speed of a vehicle, the system being operable to cause the vehicle to operate in accordance with a value of vehicle set-speed, in a first mode of operation of the system, the system being operable to apply brake torque only to one or more vehicle wheels in order to cause the vehicle to operate in accordance with a value of vehicle set-speed for the first mode and not to apply drive torque, in a second mode of operation of the system, the system being operable to apply brake torque or drive torque to one or more vehicle wheels in order to cause the vehicle to operate in accordance with a value of vehicle set-speed for the second mode.

In the first mode the system may be operable to apply brake torque in order to cause the vehicle to operate in accordance with the value of first mode set-speed only when the system determines that the vehicle is descending a slope.

Optionally the system is operable to assume the first mode when system operation is requested, when in the first mode the system being operable to assume the second mode in response to a user command to assume the second mode.

The system may be operable to assume the first mode when system operation is requested provided a speed of the vehicle is below a first mode threshold value.

Optionally if the speed of the vehicle is not below the first mode threshold value when system operation is requested, the system is configured to assume a third mode corresponding to a standby mode in which the system is not operable to apply brake torque or drive torque to the one or more vehicle wheels.

Optionally, if system operation is requested when the speed of the vehicle is above a standby mode threshold value that is greater than the first mode threshold value, the system is configured not to assume the standby mode or the first mode or the second mode.

The system may be configured to notify a user of a current operating mode, optionally via a human-machine interface. The system may in addition notify a user why the system is unable to assume the first mode. The system may provide guidance to a user as to one or more conditions that must be met in order to allow the system to assume the first mode.

Optionally, if system operation is requested when a prescribed one or more other vehicle control systems are operating, the system is operable to assume the second mode and not the first mode.

The prescribed one or more other vehicle control systems may be selected from amongst a hill descent control system, a highway cruise control system, an autonomous cruise control system and an active speed limiter control system.

By autonomous cruise control system is meant a cruise control system operable to maintain a prescribed minimum distance behind a followed vehicle when a speed of the followed vehicle is less than an autonomous cruise control system set-speed.

Optionally, when in the first mode the system is operable to assume the second mode in response to a command to increase the vehicle set-speed.

Further optionally, when in the first mode the system is operable to assume the second mode in response to a command to increase the vehicle set-speed provided the vehicle speed does not exceed a second mode upper threshold speed.

Optionally, if in response to the command to increase the vehicle set-speed the vehicle assumes the second mode, the vehicle sets the second mode set-speed to be substantially equal to the current value of vehicle speed.

Optionally, in the first mode the system is operable to apply brake torque in order to cause the vehicle to operate in accordance with the value of first mode set-speed only when the system determines that the vehicle is descending a slope and vehicle speed exceeds the first mode set-speed.

The system may be operable when in the second mode to cause the vehicle to operate in accordance with a value of vehicle set-speed by causing the vehicle to operate in accordance with the second mode set-speed.

The system may be operable when in the second mode to cause the vehicle to travel at a speed substantially equal to the second mode set-speed.

The system may be operable to limit vehicle speed in dependence on a type of terrain over which the vehicle is travelling.

The system may be operable to limit vehicle speed in dependence on terrain type determined according to a selected vehicle terrain mode.

By vehicle terrain mode is meant a mode of operation of the vehicle in which one or more vehicle sub-system operating parameters are set according to the type of terrain over which the vehicle is travelling. The modes may be referred to as terrain modes, or terrain response modes.

For example, in one embodiment one of a plurality of respective accelerator pedal/powertrain torque maps is selected in dependence on the type of terrain, such as a grass/gravel/snow terrain type, sand terrain type, and rocky terrain type. The terrain type may be detected automatically by the vehicle, or determined according to a user-operable terrain mode selector.

The may be operable wherein the first and second modes employ the same value of set-speed.

In a further aspect of the invention for which protection is sought there is provided a vehicle comprising the control system described in the immediately preceeding paragraphs.

In a still further aspect of the invention for which protection is sought there is provided a method of controlling the speed of a vehicle in accordance with a value of vehicle set-speed, the method comprising: in a first mode of operation of the system, applying brake torque only to one or more vehicle wheels to cause the vehicle to operate in accordance with a value of vehicle set-speed for the first mode and not applying drive torque; and in a second mode of operation of the system, applying brake torque or drive torque to one or more vehicle wheels to cause the vehicle to operate in accordance with a value of vehicle set-speed for the second mode.

It is to be understood that the set-speed may also be referred to herein as a 'target speed' and the terms 'target speed' and 'set-speed' are used interchangeably herein.

It will be appreciated that preferred and/or optional features of any one aspect of the invention may be incorporated alone or in appropriate combination within the any other aspect of the invention also.

BRIEF DESCRIPTION OF THE DRAWINGS

The invention will now be described by way of example only with reference to the following figures in which.

DETAILED DESCRIPTION

The content of co-pending UK patent application no GB1214651.0 is hereby incorporated by reference.

References herein to a block such as a function block are to be understood to include reference to software code for performing the function or action specified in which an output is provided responsive to one or more inputs. The code may be in the form of a software routine or function called by a main computer program, or may be code forming part of a flow of code not being a separate routine or function. Reference to function block is made for ease of explanation of the manner of operation of the controller.

Figure 1:
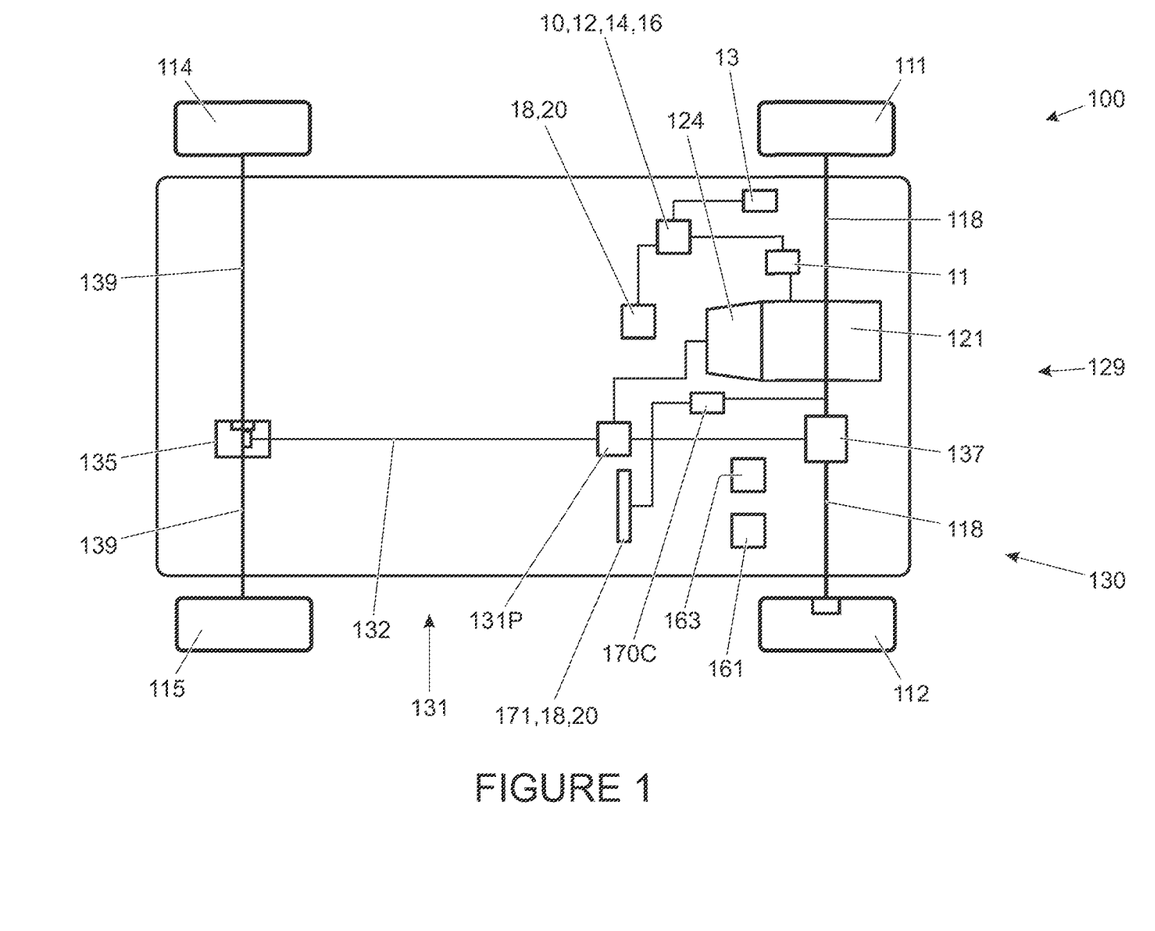
FIG. 1 is a schematic illustration of a vehicle according to an embodiment of the invention in plan view.
Figure 2:
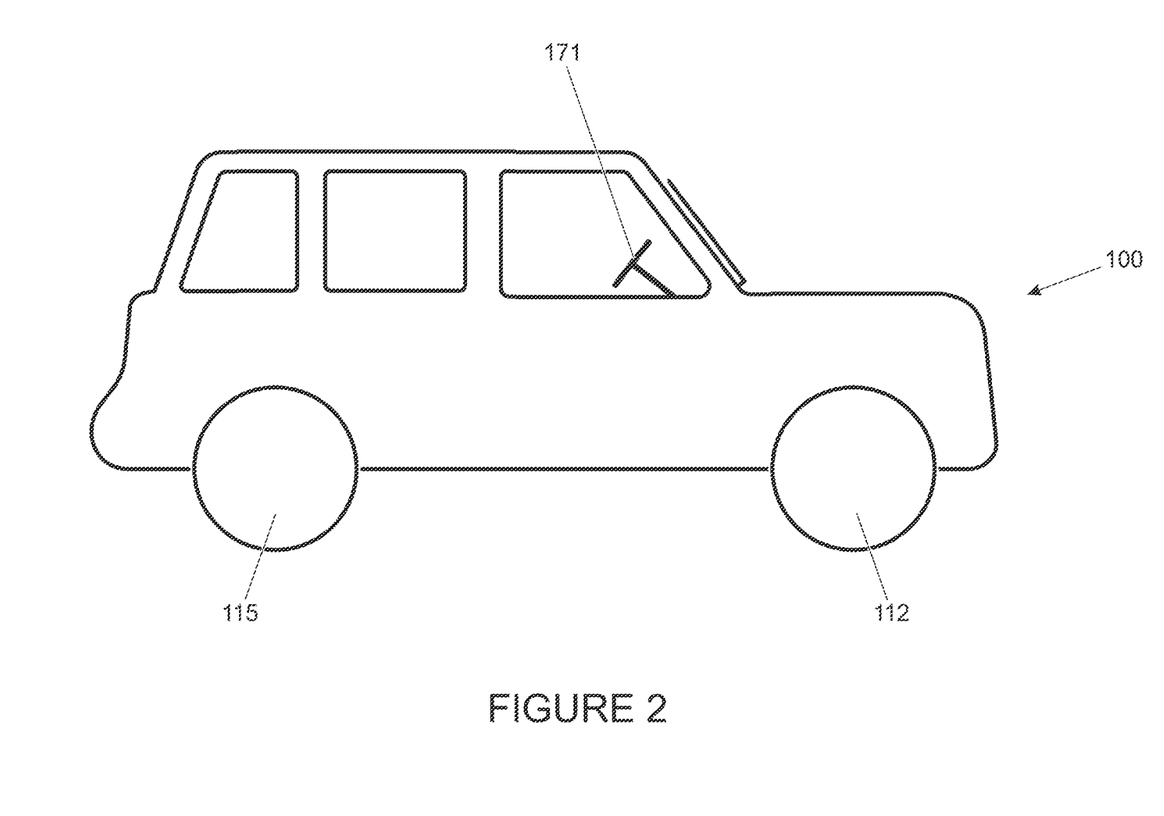
FIG. 2 shows the vehicle of FIG. 1 in side view.

FIG. 1 shows a vehicle 100 according to an embodiment of the invention having a powertrain 129. The powertrain 129 includes an engine 121 that is connected to a driveline 130 having an automatic transmission 124. Embodiments of the present invention are also suitable for use in vehicles with manual transmissions, continuously variable transmissions or any other suitable transmission.

The driveline 130 is arranged to drive a pair of front vehicle wheels 111, 112 by means of a front differential 137 and a pair of front drive shafts 118. The driveline 130 also comprises an auxiliary driveline portion 131 arranged to drive a pair of rear wheels 114, 115 by means of an auxiliary driveshaft or propshaft 132, a rear differential 135 and a pair of rear driveshafts 139. Embodiments of the invention are also suitable for use with vehicles in which the transmission is arranged to drive only a pair of front wheels or only a pair of rear wheels (i.e. front wheel drive vehicles or rear wheel drive vehicles) or selectable two wheel drive/four wheel drive vehicles. In the embodiment of FIG. 1 the transmission 124 is releasably connectable to the auxiliary driveline portion 131 by means of a power transfer unit (PTU) 131P, allowing selectable two wheel drive or four wheel drive operation. It is to be understood that embodiments of the invention may be suitable for vehicles having more than four wheels or where only two wheels are driven, for example two wheels of a three wheeled vehicle or four wheeled vehicle or a vehicle with more than four wheels.

Figure 3:
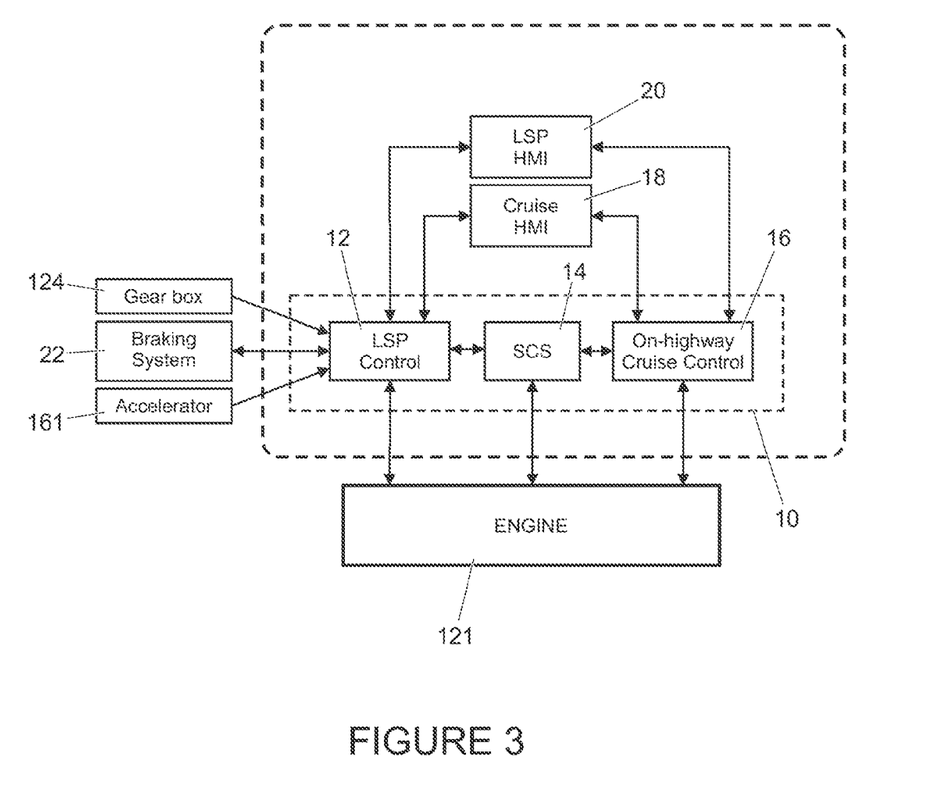
FIG. 3 is a high level schematic diagram of an embodiment of the vehicle speed control system of the present invention, including a cruise control system and a low-speed progress control system.

A control system for the vehicle engine 121 includes a central controller, referred to as a vehicle control unit (VCU) 10, a powertrain controller 11, a brake controller 13 and a steering controller 170C. The brake controller 13 forms part of a braking system 22 (FIG. 3). The VCU 10 receives and outputs a plurality of signals to and from various sensors and subsystems (not shown) provided on the vehicle. The VCU 10 includes a low-speed progress (LSP) control system 12 shown in FIG. 3 and a stability control system (SCS) 14, the latter being a known component of existing vehicle control systems. The SCS 14 improves the safety of the vehicle 100 by detecting and managing loss of traction. When a reduction in traction or steering control is detected, the SCS 14 is operable automatically to command a brake controller 13 to apply one or more brakes of the vehicle to help to steer the vehicle 100 in the direction the user wishes to travel. In the embodiment shown the SCS 14 is implemented by the VCU 10. In some alternative embodiments the SCS 14 may be implemented by the brake controller 13. Further alternatively, the SCS 14 may be implemented by a separate controller.

Although not shown in detail in FIG. 3, the VCU 10 further includes a Dynamic Stability Control (DSC) function block, a Traction Control (TC) function block, an Anti-Lock Braking System (ABS) function block and a Hill Descent Control (HDC) function block. These function blocks are implemented in software code run by a computing device of the VCU 10 and provide outputs indicative of, for example, DSC activity, TC activity, ABS activity, brake interventions on individual wheels and engine torque requests from the VCU 10 to the engine 121 in the event a wheel slip event occurs. Each of the aforementioned events indicate that a wheel slip event has occurred. Other vehicle sub-systems such as a roll stability control system or the like may also be useful.

Figure 6:
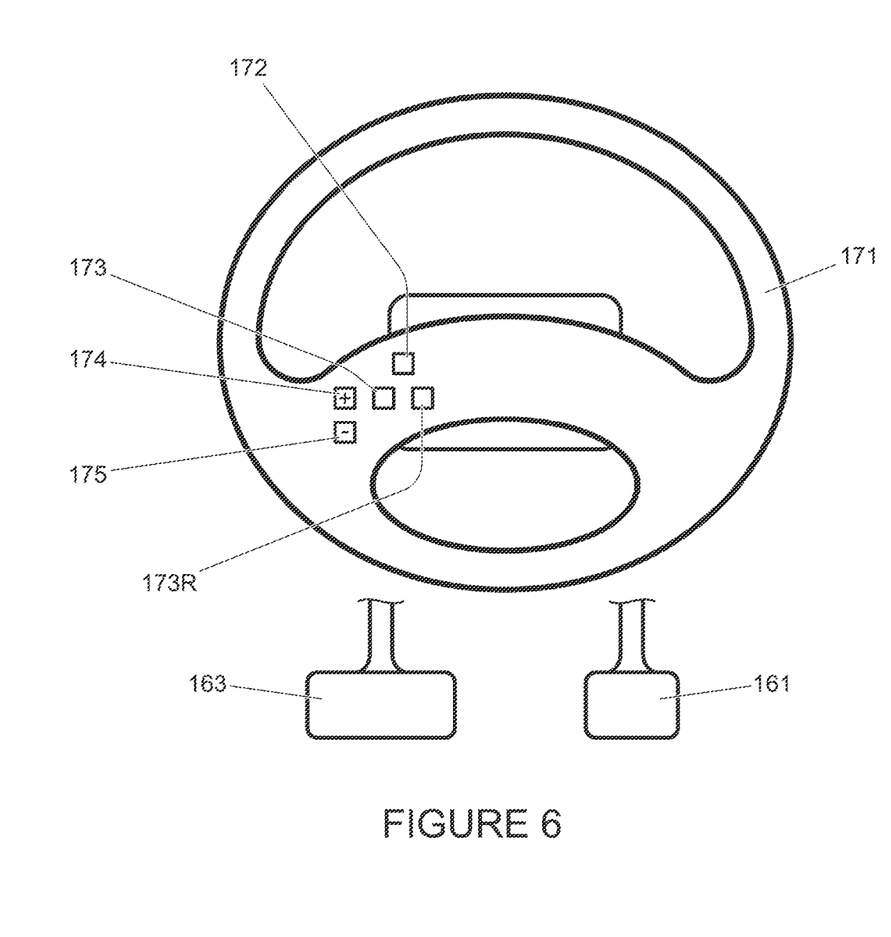
FIG. 6 illustrates a steering wheel and brake and accelerator pedals of a vehicle according to an embodiment of the present invention.

The vehicle 100 also includes a cruise control system 16 which is operable to automatically maintain vehicle speed at a selected speed when the vehicle is travelling at speeds in excess of 30 kph. The cruise control system 16 is provided with a cruise control HMI (human machine interface) 18 by which means the user can input a target vehicle speed to the cruise control system 16 in a known manner. In one embodiment of the invention, cruise control system input controls are mounted to a steering wheel 171 (FIG. 6). Depression of a 'set-speed' control 173 sets the set-speed to the current vehicle speed. Depression of a '+' button 174 allows the set-speed to be increased whilst depression of a '−' button 175 allows the set-speed to be decreased. In some embodiments, if the cruise control system 16 is not active when the '+' button 174 is depressed, the cruise control system 16 is activated.

The cruise control system 16 monitors vehicle speed and any deviation from the target vehicle speed is adjusted automatically so that the vehicle speed is maintained at a substantially constant value, typically in excess of 30 kph. In other words, the cruise control system is ineffective at speeds lower than 30 kph. The cruise control HMI 18 may also be configured to provide an alert to the user about the status of the cruise control system 16 via a visual display of the HMI 18.

The LSP control system 12 provides a speed-based control system for the user which enables the user to select a very low target speed at which the vehicle can progress without any pedal inputs being required by the user. This low-speed progress control function is not provided by the on-highway cruise control system 16 which operates only at speeds above 30 kph. Furthermore, known on-highway cruise control systems including the present system 16 are configured so that, in the event that the user depresses the brake or the clutch, the cruise control function is cancelled and the vehicle 100 reverts to a manual mode of operation which requires user pedal input to maintain vehicle speed. In addition, detection of a wheel slip event, as may be initiated by a loss of traction, also has the effect of cancelling the cruise control system 16 function.

The LSP control system 12 is operable to apply selective powertrain, traction control and braking actions to the wheels of the vehicle, collectively or individually, to maintain the vehicle 100 at the desired speed. It is to be understood that if the vehicle 100 is operating in a two wheel drive mode in which only front wheels 111, 112 are driven, the control system 12 may be prevented from applying drive torque to rear wheels 113, 114 of the vehicle 100.

The user inputs the desired target speed to the LSP control system 12 via a low-speed progress control HMI (LSP HMI) 20 (FIG. 1, FIG. 3). The LSP control system 12 operates at vehicle speeds typically below about 50 kph but does not activate until vehicle speed drops to below 30 kph when the cruise control system of the vehicle becomes ineffective. The LSP control system 12 is configured to operate independently of a traction event, i.e. the system 12 does not cancel speed control upon detection of wheel slip. Rather, the LSP control system 12 actively manages vehicle behaviour and in this way, at least, differs from the functionality of the cruise control system 16, as will be described in further detail below.

The LSP control HMI 20 is provided in the vehicle cabin so as to be readily accessible to the user. The user of the vehicle is able to input to the LSP control system 12, via the LSP HMI 20, an indication of the speed at which the user desires the vehicle to travel (referred to as "the target speed"). The LSP HMI 20 also includes a visual display upon which information and guidance can be provided to the user about the status of the LSP control system 12.

The LSP control system 12 receives an input from the braking system 22 of the vehicle indicative of the extent to which the user has applied braking by means of a brake pedal 163. The LSP control system 12 also receives an input from an accelerator pedal 161 indicative of the extent to which the user has depressed the accelerator pedal 161. An input is also provided to the LSP control system 12 from the transmission or gearbox 124. This input may include signals representative of, for example, the speed of an output shaft of the gearbox 124, torque converter slip and a gear ratio request. Other inputs to the LSP control system 12 include an input from the cruise control HMI 18 which is representative of the status (ON/OFF) of the cruise control system 16, and an input from the LSP control HMI 20 which is representative of the status of the LSP control function.

The cruise control HMI 18 and the LSP HMI 20 have input controls provided on a steering wheel of the vehicle for convenience of operation by the user.

FIG. 6 shows the steering wheel 171 of the vehicle 100 of FIG. 1 in more detail, together with the accelerator and brake pedals 161, 163. As noted above, the steering wheel 171 bears user operable input controls of the cruise control HMI 18 and LSP control HMI 20. As in the case of a conventional vehicle, the steering wheel 171 has a 'set-speed' control 173, actuation of which enables a user to activate the cruise control system 16 to maintain the current vehicle speed. The wheel 171 also has a 'LSP' control activation button 172 for activating the LSP control system 12 and a resume button 173R. The resume button 173R may be used to control both the 'on-highway' cruise control system 16 when driving on road, and the LSP control system 12 when driving off-road, to resume a previously set (user defined) set-speed.

If the vehicle is operating on-highway, depression of set-speed control 173 causes the cruise control system 16 to activate provided the current vehicle speed is within the operating range of the cruise control system 16. Depression of the '+' control 174 causes the cruise control system 16 to increase the set-speed whilst depression of the '−' control 175 causes the cruise control system 16 to decrease the set-speed. It will be appreciated that '+' and '−' controls may be on a single button in some arrangements, such as a rocker-type button. In some embodiments, the '+' control 174 may function as a 'set-speed' control, in which case set-speed control 173 may be eliminated.

If the vehicle is operating off-highway, depression of set-speed control 173 causes the LSP control system 12 to activate and operate as described above, provided vehicle speed is within the operating range of the LSP control system 12.

In some embodiments. the system may further comprise a 'cancel' button operable to cancel speed control by the LSP control system 12. In some embodiments, the LSP system may be in either one of an active condition or a standby condition. In the present embodiment the LSP control system 12 is also operable to assume an intermediate condition in which vehicle speed control by the LSP control system 12 is suspended but a hill descent control (HDC) system or the like may remain active if already active. Other arrangements are also useful.

With the LSP control system 12 active, the user may increase or decrease the vehicle set-speed by means of the '+' and '−' buttons 174, 175. In addition, the user may also increase or decrease the vehicle set-speed by lightly pressing the accelerator or brake pedals 161, 163 respectively. In some embodiments, with the LSP control system 12 active the '+' and '−' buttons 174, 175 are disabled. This latter feature may prevent changes in set-speed by accidental pressing of one of these buttons, for example when negotiating difficult terrain where relatively large and frequent changes in steering angle may be required. Other arrangements are also useful.

Figure 4:
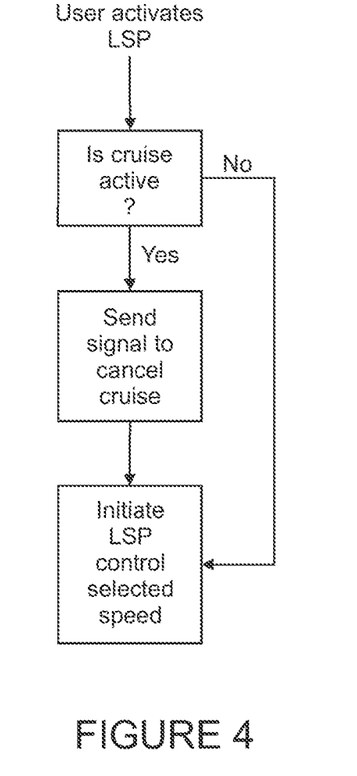
FIG. 4 is a flow diagram to illustrate the interaction between the cruise control system and the low-speed progress control system in FIG. 3.

FIG. 4 shows a flow process to illustrate the interaction between the cruise control system 18 and the LSP control system 12. If cruise control is active when the user tries to activate the LSP control system 12 via the LSP control HMI 20, a signal is sent to the cruise control system 16 to cancel the speed control routine. The LSP control system 12 is then initiated and the vehicle speed is maintained at the target speed selected by the user via the LSP HMI 20. It is also the case that if the LSP control system 12 is active, operation of the cruise control system 16 is inhibited. The two systems 12, 16 therefore operate independently of one another, so that only one can be operable at any one time, depending on the speed at which the vehicle is travelling.

In some embodiments, the cruise control system 16 may hand over vehicle speed control to the LSP control system 12 if a user reduces set-speed of the vehicle 100 to a value within the operating speed range of the LSP control system 12. Similarly, in some embodiments the LSP control system 16 may hand over vehicle speed control to the cruise control system 16 if a user raises vehicle set-speed to a value that is within the operating range of the cruise control system 16. Other arrangements are also useful.

In some embodiments, the cruise control HMI 18 and the LSP control HMI 20 may be configured within the same hardware so that, for example, the speed selection is input via the same hardware, with one or more separate switches being provided to switch between the LSP input and the cruise control input.

Figure 5:
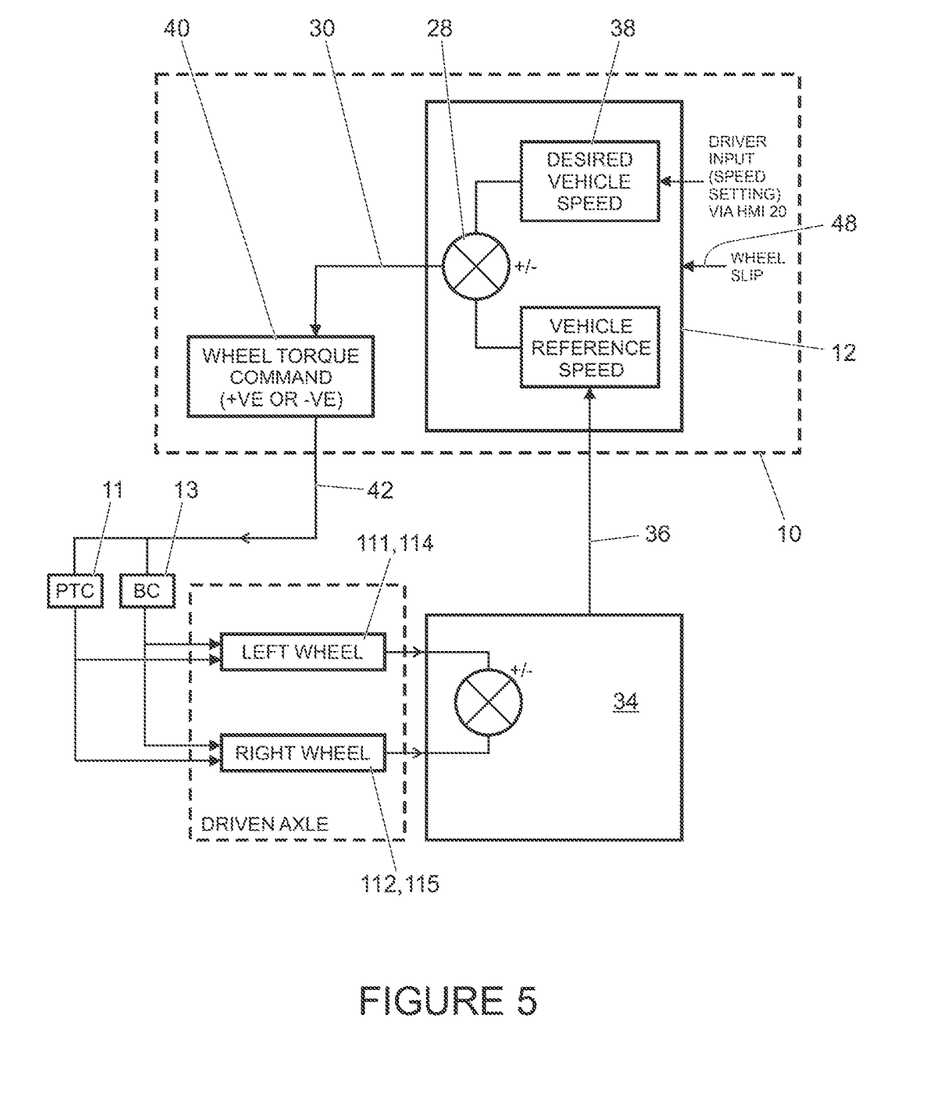
FIG. 5 is a schematic diagram of further features of the vehicle speed control system in FIG. 3.

FIG. 5 illustrates the means by which vehicle speed is controlled in the LSP control system 12. As described above, a speed selected by a user (set-speed) is input to the LSP control system 12 via the LSP control HMI 20. A vehicle speed sensor 34 associated with the powertrain 129 (shown in FIG. 1) provides a signal 36 indicative of vehicle speed to the LSP control system 12. The LSP control system 12 includes a comparator 28 which compares the set-speed (also referred to as a 'target speed' 38) selected by the user with the measured speed 36 and provides an output signal 30 indicative of the comparison. The output signal 30 is provided to an evaluator unit 40 of the VCU 10 which interprets the output signal 30 as either a demand for additional torque to be applied to the vehicle wheels 111-115, or for a reduction in torque applied to the vehicle wheels 111-115, depending on whether the vehicle speed needs to be increased or decreased to maintain the speed that has been selected by the user. An increase in torque is generally accomplished by increasing the amount of powertrain torque delivered to a given position of the powertrain, for example an engine output shaft, a wheel or any other suitable location. A decrease in torque to a value that is less positive or more negative may be accomplished by decreasing powertrain torque delivered to a wheel and/or by increasing a braking force on a wheel. It is to be understood that in some embodiments in which a powertrain 129 has an electric machine operable as a generator, negative torque may be applied by the powertrain 129 to one or more wheels. It is to be understood that a brake controller 13 may nevertheless be involved in determining whether brake torque is required to be provided by an electric machine of a powertrain 129, and whether brake torque should be provided by an electric machine or a friction-based foundation braking system 22.

An output 42 from the evaluator unit 40 is provided to the powertrain controller 11 and brake controller 13 which in turn control a net torque applied to the vehicle wheels 111-115. The net torque may be increased or decreased depending on whether there is a positive or negative demand for torque from the evaluator unit 40. Thus, in order to initiate application of the necessary positive or negative torque to the wheels, the evaluator unit 40 may command that additional power is applied to the vehicle wheels and/or that a braking force is applied to the vehicle wheels, either or both of which may be used to implement the change in torque that is necessary to maintain the target vehicle speed. In the illustrated embodiment the torque is applied to the vehicle wheels individually so as to maintain the target vehicle speed, but in another embodiment torque may be applied to the wheels collectively to maintain the target speed. In some embodiments, the powertrain controller 11 may be operable to control an amount of torque applied to one or more wheels by controlling a driveline component such as a rear drive unit, front drive unit, differential or any other suitable component. For example, one or more components of the driveline 130 may include one or more clutches operable to allow an amount of torque applied to one or more wheels to be varied. Other arrangements are also useful.

Where a powertrain 129 includes one or more electric machines, for example one or more propulsion motors and/or generators, the powertrain controller 11 may be operable to modulate torque applied to one or more wheels by means of one or more electric machines. In some embodiments, the one or more electric machines may be operable as either a propulsion motor or a generator under the control of the powertrain controller 11. Thus the powertrain controller 11 may in some embodiments be controlled to apply more positive or more negative torque to one or more wheels by means of an electric machine.

The LSP control system 12 also receives a signal 48 indicative of a wheel slip event having occurred. This may be the same signal 48 that is supplied to the on-highway cruise control system 16 of the vehicle, and which in the case of the latter triggers an override or inhibit mode of operation in the on-highway cruise control system 16 so that automatic control of the vehicle speed by the on-highway cruise control system 16 is suspended or cancelled. However, the LSP control system 12 is not arranged to cancel or suspend operation in dependence on receipt of a wheel slip signal 48 indicative of wheel slip. Rather, the system 12 is arranged to monitor and subsequently manage wheel slip so as to reduce driver workload. During a slip event, the LSP control system 12 continues to compare the measured vehicle speed with the desired vehicle speed as input by the user, and continues to control automatically the torque applied across the vehicle wheels so as to maintain vehicle speed at the selected value. It is to be understood therefore that the LSP control system 12 is configured differently to the cruise control system 16, for which a wheel slip event has the effect of overriding the cruise control function so that manual operation of the vehicle must be resumed, or the cruise control function reset.

A further embodiment of the invention (not shown) is one in which the vehicle is provided with a wheel slip signal 48 derived not just from a comparison of wheel speeds, but further refined using sensor data indicative of the vehicle's speed over ground. Such speed over ground determination may be made via global positioning (GPS) data, or via a vehicle mounted radar or laser based system arranged to determine the relative movement of the vehicle and the ground over which it is travelling. A camera system may be employed for determining speed over ground in some embodiments.

At any stage of the LSP control process the user can override the function by depressing the accelerator pedal 161 and/or brake pedal 163 to adjust the vehicle speed in a positive or negative sense. However, in the event that a wheel slip event is detected via signal 48, the LSP control system 12 remains active and control of vehicle speed by the LSP control system 12 is not suspended. As shown in FIG. 5, this may be implemented by providing a wheel slip event signal 48 to the LSP control system 12 which is then managed by the LSP control system 12. In the embodiment shown in FIG. 1 the SCS 14 generates the wheel slip event signal 48 and provides it to the LSP control system 12 and cruise control system 16.

A wheel slip event is triggered when a loss of traction occurs at any one of the vehicle wheels. Wheels and tyres may be more prone to losing traction when travelling on snow, ice, mud or sand and/or on steep gradients or cross-slopes, for example, or in environments where the terrain is more uneven or slippery compared with driving on a highway in normal on-road conditions. Embodiments of the present invention therefore find particular benefit when the vehicle is being driven in an off-road environment, or in conditions in which wheel slip may commonly occur. Manual operation by the user in such conditions can be a difficult and often stressful experience and may result in an uncomfortable ride. Embodiments of the present invention enable continued progress to be made at a relatively low target speed without the need for user intervention.

The vehicle 100 is also provided with additional sensors (not shown) which are representative of a variety of different parameters associated with vehicle motion and status. These may be inertial systems unique to the speed control system or part of an occupant restraint system or any other sub-system which may provide data from sensors such as gyros and/or accelerometers that may be indicative of vehicle body movement and may provide a useful input to the LSP control system 12. The signals from the sensors provide, or are used to calculate, a plurality of driving condition indicators (also referred to as terrain indicators) which are indicative of the nature of the terrain conditions over which the vehicle is travelling. The signals are provided to the VCU 10 which determines the most appropriate control mode for the various subsystems on the basis of the terrain indicators, and automatically controls the subsystems accordingly. This aspect of the invention is described in further detail in our co-pending patent application nos. GB1111288.5, GB1211910.3 and GB1202427.9, the contents of each of which is incorporated herein by reference.

The sensors (not shown) on the vehicle include, but are not limited to, sensors which provide continuous sensor outputs to the VCU 10, including wheel speed sensors, as mentioned previously and as shown in FIG. 5, an ambient temperature sensor, an atmospheric pressure sensor, tyre pressure sensors, wheel articulation sensors, gyroscopic sensors to detect vehicular yaw, roll and pitch angle and rate, a vehicle speed sensor, a longitudinal acceleration sensor, an engine torque sensor (or engine torque estimator), a steering angle sensor, a steering wheel speed sensor, a gradient sensor (or gradient estimator), a lateral acceleration sensor which may be part of the stability control system (SCS), a brake pedal position sensor, a brake pressure sensor, an accelerator pedal position sensor, longitudinal, lateral and vertical motion sensors, and water detection sensors forming part of a vehicle wading assistance system (not shown). In other embodiments, only a selection of the aforementioned sensors may be used.

The VCU 10 also receives a signal from the steering controller 170C. The steering controller is in the form of an electronic power assisted steering unit (ePAS unit). The steering controller 170C provides a signal to the VCU 10 indicative of the steering force being applied to steerable road wheels 111, 112 of the vehicle 100. This force corresponds to that applied by a user to the steering wheel 171 in combination with steering force generated by the controller 170C.

The VCU 10 evaluates the various sensor inputs to determine the probability that each of a plurality of different control modes for the vehicle subsystems is appropriate, with each control mode corresponding to a particular terrain type over which the vehicle is travelling (for example, mud and ruts, sand, grass/gravel/snow). The VCU 10 then selects which of the control modes is most appropriate and controls various vehicle parameters accordingly.

The nature of the terrain over which the vehicle is travelling (as determined by reference to the selected control mode) may also be utilised in the LSP control system 12 to determine an appropriate increase or decrease in drive torque to be applied to the vehicle wheels. For example, if the user selects a target speed that is not suitable for the nature of the terrain over which the vehicle is travelling, the system 12 is operable to automatically adjust the vehicle speed downwards by reducing the speed of the vehicle wheels. In some cases, for example, the user selected speed may not be achievable or appropriate over certain terrain types, particularly in the case of uneven or rough surfaces. If the system 12 selects a set-speed that differs from the user-selected set-speed (i.e. target speed), a visual indication of the speed constraint is provided to the user via the LSP HMI 20 to indicate that an alternative speed has been adopted.

Figure 7:
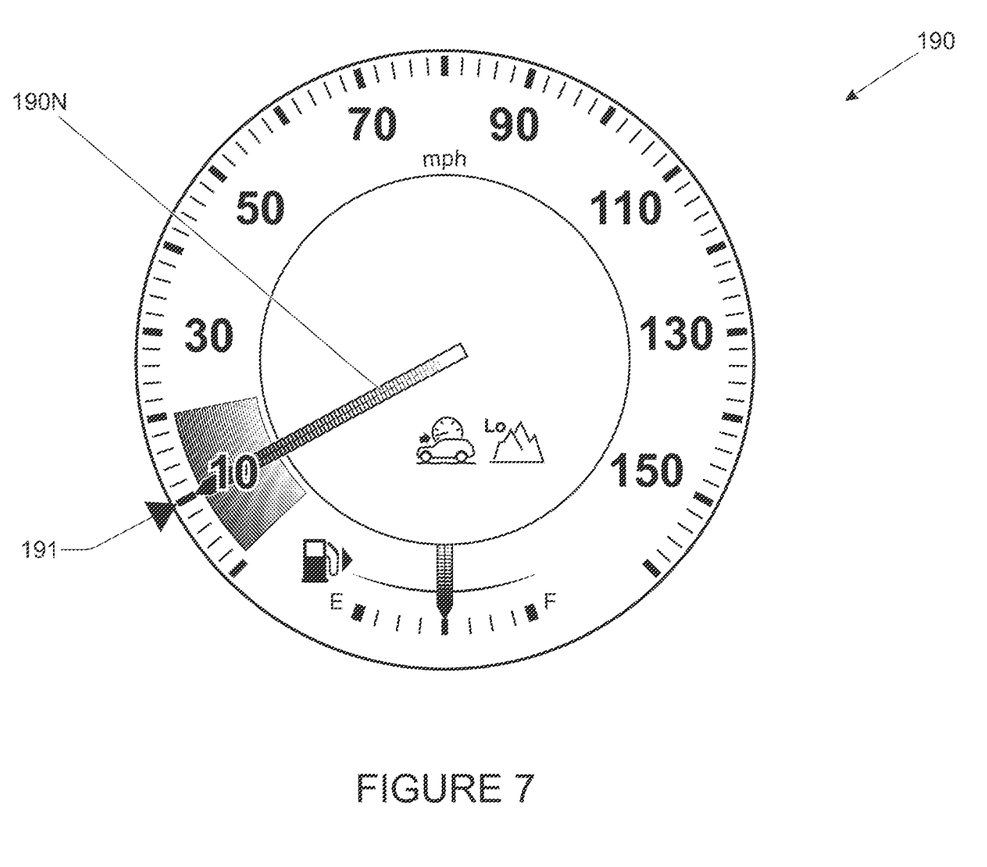
FIG. 7 and FIG. 8 show examples of a speedometer display of the vehicle of FIG. 1 at different times during vehicle operation.

As shown in FIG. 7, the vehicle 100 has a speedometer 190 operable to indicate by means of a pointer or needle 190N a speed of the vehicle on a gauge having speed markings in prescribed increments. When the LSP control system 12 is operational, a 'current set-speed' illuminated marker or chaplet 191 is displayed on the speedometer 190 at a location corresponding to the current set-speed. In the embodiment shown the marker is provided at a circumferential angular position corresponding to the expected position of the needle 190N when the vehicle is travelling at the set-speed. In the example illustrated in FIG. 7 the speedometer is indicating a current vehicle speed of 10 mph, and a current set-speed of 10 mph.

In the present embodiment the speedometer 190 is provided in the form of a graphical display on an electronic display panel and is generated electronically by a computing device. In some alternative embodiments the speedometer 190 may be in the form at least in part of a mechanical system having a physical needle rotatable around an axis.

The speedometer 190 is arranged to display the 'current set-speed' chaplet 191 in a prescribed colour and with relatively bright illumination.

As described above, with the LSP control system 12 active, the user may increase or decrease the vehicle set-speed by means of the '+' and '−' buttons 174, 175. These buttons 174, 175 may also be referred to as 'set +' and 'set −' buttons 174, 175.

When the user changes the set-speed in this manner, the 'current set-speed' chaplet 191 moves in a circumferential manner to a radial position corresponding to the new value of current set-speed.

As also described above, the user may also increase or decrease the value of current set-speed by lightly pressing the accelerator or brake pedals 161, 163 respectively. In the present embodiment, if the user decreases the value of current set-speed by depressing the brake pedal 163 by an amount within a prescribed range, the 'current set-speed' chaplet moves to indicate a lower speed in the expected manner. It is to be understood that in some embodiments, instead of brake pedal position, if the amount of brake pressure is within a prescribed range the 'current set-speed' chaplet moves to indicate a lower speed. Further application of brake pressure would result in cancellation of speed control. The prescribed range (whether of pedal position or brake pressure) may be a range corresponding to application of up to 5% of maximum available braking torque. Above this value, speed control may be cancelled.

It is to be understood that a 'dead-band' may exist in respect of brake pedal position such that as a driver begins to apply pressure to the brake pedal 163, brakes are not applied until the pressure applied (or the amount by which the pedal has been moved from a released position) exceeds a prescribed amount. Alternatively or in addition, the system 12 may be configured to apply an amount of positive drive torque in response to a detected user input via the brake pedal to compensate for brake torque applied if the pedal displacement or applied pedal pressure is below a pre-determined threshold. This may be accomplished for example by pre-charging the braking system upon detection of a pedal input, but applying a small amount of positive torque to compensate for the slight negative (brake) torque applied to the wheels.

In the present embodiment, if the user commands a reduction in set-speed by lightly depressing the brake pedal 163 the control system 12 stores the current value of set-speed in memory as a second set-speed, and then decreases the current value of set-speed according to the user command. The 'current set-speed' chaplet 191 moves to indicate a lower speed in a corresponding manner as described above. An example scenario is shown in FIG. 8 where a user has used the brake pedal 163 to reduce the current value of set-speed from a value of 10 mph to a value of substantially 5 mph.

Figure 8:
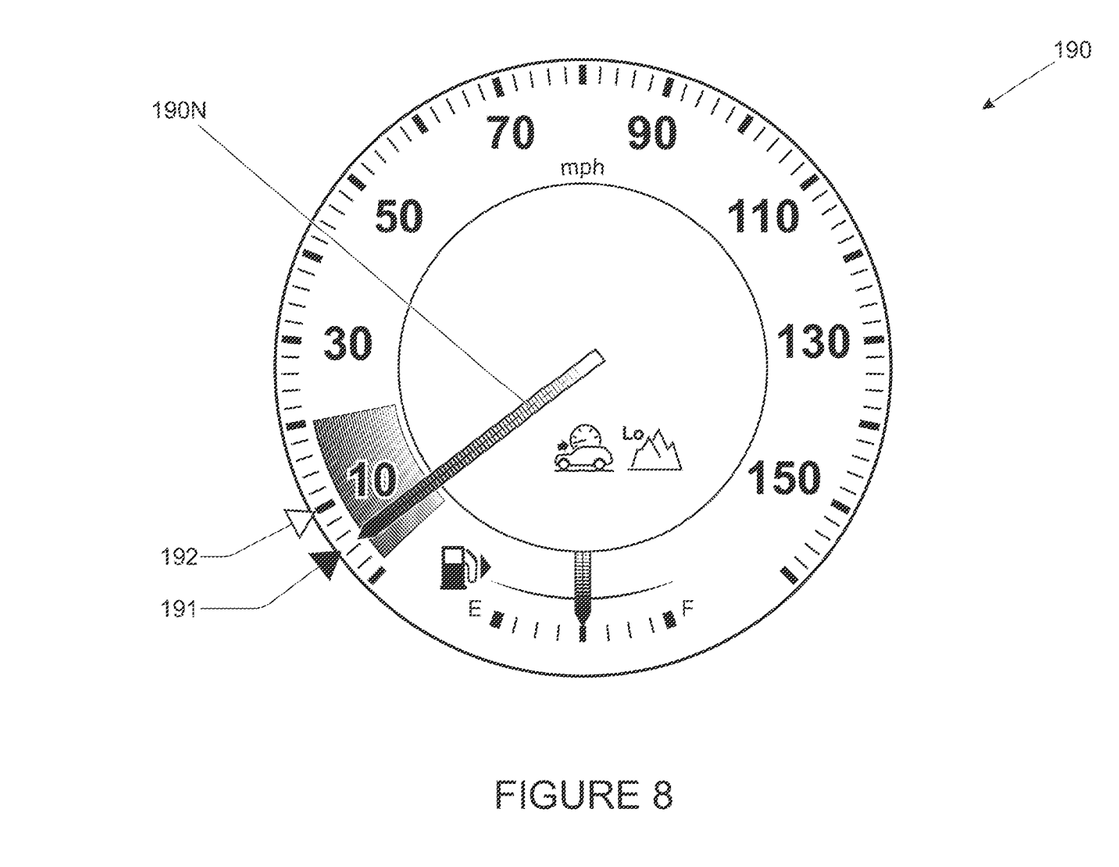

In addition, a second chaplet 192 is displayed at a position of the speedometer 190 corresponding to the second set-speed, as shown in FIG. 8. That is, the second chaplet 192 is displayed at the location of the 'current set-speed' chaplet 191 at the moment when the driver commanded the reduction in set-speed. In the present embodiment the second chaplet 192 corresponds to a wire frame outline, or 'ghost' of the 'current set-speed' chaplet 191.

If the user depresses the 'resume' button 173R within a prescribed time period of ceasing depression of the brake pedal 163, the control system 12 sets the current value of set-speed to the second set-speed and controls the vehicle in a corresponding manner. That is, the control system 12 may attempt to accelerate the vehicle to the second set-speed. In some embodiments, the control system 12 attempts to accelerate the vehicle to the second set-speed only if one or more prescribed conditions are met.

If the user does not depress the resume button 173R within the prescribed period, the control system 12 no longer displays the second chaplet 192, and no longer permits the value of current set-speed to be set to the second set-speed if the user presses the resume button 173R.

The vehicle 100 is configured to allow a user to select speed control by the LSP control system 12 by means of 'LSP' control activation button 172 as described above. When LSP button 172 is pressed, the LSP control system activates in dependence on a current value of vehicle speed.

Figure 9:
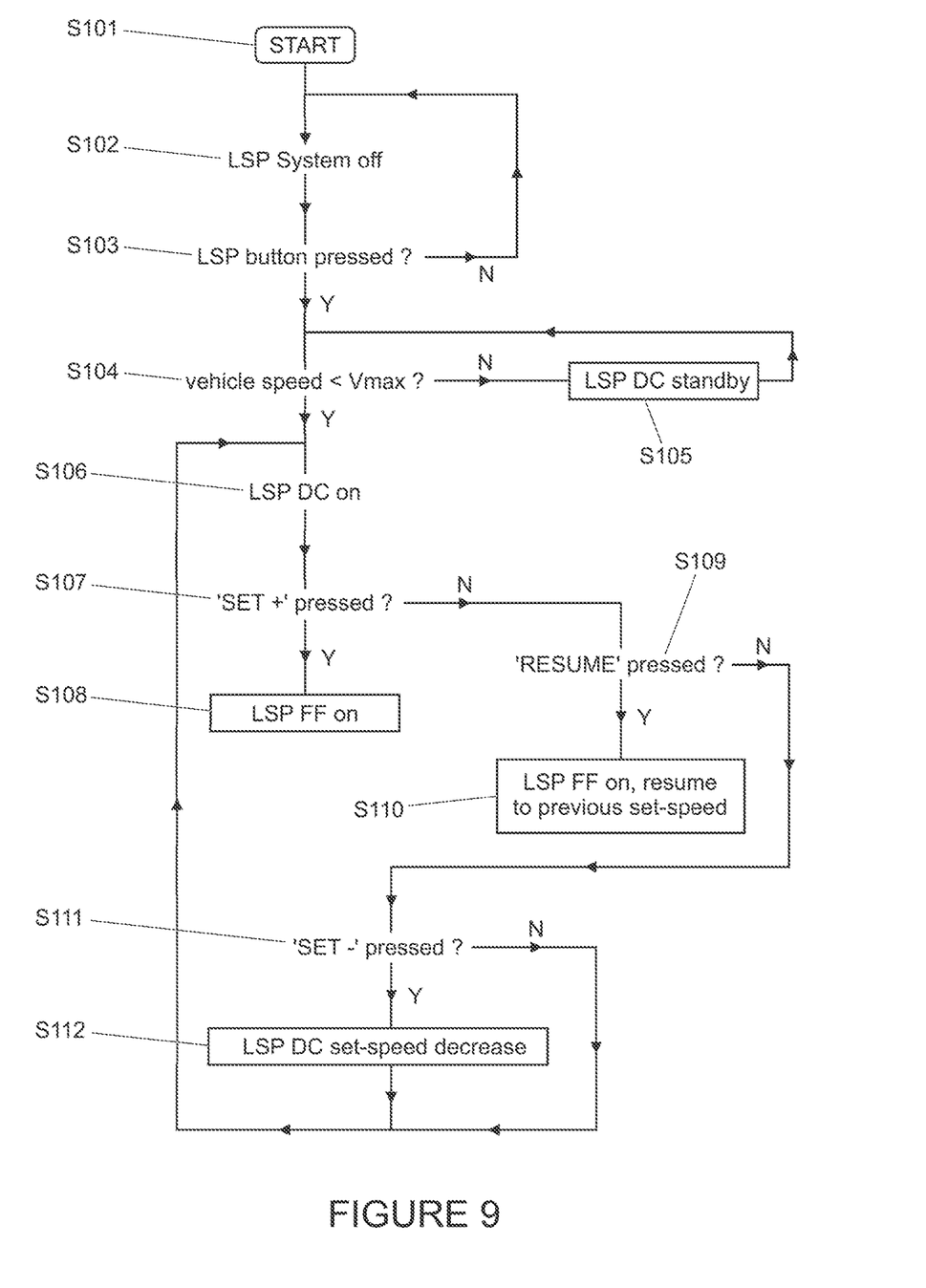
FIG. 9 is a flow diagram illustrating operation of a speed control system according to an embodiment of the present invention.

FIG. 9 is a flow diagram illustrating operation of the LSP control system 12.

At step S102 the LSP control system 12 is in an 'OFF' condition. At step S103 the system 12 determines whether a user has depressed the LSP button 172 in attempt to activate the LSP control system 12 to perform vehicle speed control.

If at step S103 the system 12 detects that the LSP button 172 has been pressed, then at step S104 the system 12 determines whether vehicle speed is below a prescribed upper LSP control system operating threshold, vmax. In the present embodiment vmax is substantially equal to 30 mph although other speeds are also useful.

If at step S104 the system 12 determines that the vehicle speed is not less than vmax, the system repeats step S104, but first continues at step S105 and assumes an LSP descent control (DC) standby mode. In the LSP DC standby mode the system 12 is prevented from assuming the LSP DC mode, and remains in a standby mode in which the LSP control system does not perform speed control. The LSP control system 12 repeats step S104 until vehicle speed falls below vmax.

If at step S104 the vehicle speed is less than vmax, the system continues at step S106 and the LSP control system 12 assumes operation in a first mode. In the present embodiment the first mode corresponds to a descent control (DC) mode in which the LSP control system 12 is operable to apply a braking system of the vehicle 100 to prevent vehicle speed exceeding a set-speed corresponding to operation in the first mode. However in the first mode the system 12 is not permitted to apply positive drive torque to maintain the set-speed if vehicle speed falls below the first mode set-speed.

At step S107 the LSP control system 12 determines whether a user has requested an increase in set-speed. If the user has requested an increase in set-speed, for example by depressing the 'set +' button 174, the system 12 continues to step S108 and assumes a second mode. In the present embodiment the second mode corresponds to a mode in which the LSP control system 12 is operable to command application of positive drive torque and/or negative torque (such as brake torque) to one or more vehicle wheels in order to control the vehicle 100 to maintain the current speed of the vehicle. In other words, the set-speed of the LSP control system 12 is set to be substantially equal to the current speed of the vehicle. If the system 12 determines that the current speed is not appropriate to the prevailing terrain the system may set the value of set-speed to the current speed but control the vehicle 100 to travel at a reduced value of set-speed until the user selected value of set-speed is determined to be appropriate to the prevailing terrain. The second mode may also be referred to as an LSP control system 'full-functionality' (FF) mode, since application of positive drive torque is not prevented when in the second mode.

If at step S107 it is determined that the 'set +' button has not been pressed, then at step S109 the system determines whether the 'resume' button 173R has been pressed. If the system determines that the resume button 173R has been pressed, then at step S110 the LSP control system 12 assumes the second mode and sets the value of set-speed to be equal to a previously selected value of set-speed. This value is typically a value of set-speed currently stored by the LSP control system 12.

The LSP control system 12 may set the current set-speed to be substantially equal to a value of set-speed selected when the system was most recently in the second mode. If when the system was most recently in the second mode a second set-speed value was stored in memory and operation in the second mode was cancelled before expiry of the prescribed period for resumption of operation at the second set-speed, the system 12 may set the current value of set-speed to the second set-speed value. Other arrangements are also useful.

If at step S109 it is determined that the resume button 173R has not been pressed, then at step S111 it is determined whether the 'set –' button has been pressed. If the 'set –' button has been pressed, then the first mode set-speed is decremented accordingly.

If the 'set –' button has not been pressed, the system continues at S106.

In some embodiments, if the LSP control system 12 automatically selects a temporarily reduced speed, for example in response to prevailing terrain, the system 12 may be arranged to provide an indication on the speedometer 190 of the new, temporarily reduced set-speed. The indication may be in the form of a further chaplet. Thus, in some embodiments the system 12 may display the 'current set-speed' chaplet 191, the second chaplet 192, and a chaplet corresponding to the temporarily reduced set-speed. This feature provides the user with a clear indication that the LSP control system 12 is operating correctly and that the reduction in set-speed is intentional. This may enhance user confidence in the LSP control system 12.

In some embodiments, the 'current set-speed' chaplet 191 may indicate the temporarily reduced set-speed whilst a further chaplet indicates the set-speed at which the user has selected vehicle operation.

Other arrangements are also useful.

The above description in combination with FIG. 9 is intended to illustrate only some aspects of operation of the LSP control system 12. It is to be understood that the order in which some of the steps described above are performed may be different in some embodiments, such as steps S107, S109 and step S111.

In some embodiments of the present invention, if a speed of the vehicle 100 exceeds the current value of set-speed, the LSP control system 12 is operable to apply braking to reduce the speed of the vehicle in response to a user request. In one embodiment, if the user depresses the 'set –' button 175 a prescribed number of times, for example three times in one embodiment, the control system 12 applies brake torque to slow the vehicle 100. The control system 12 may apply brake torque to slow the vehicle 100 to the current set-speed in some embodiments. In some embodiments, when the user requests braking to slow the vehicle 100 in this manner the control system 12 does not change the value of set-speed.

This feature may be particularly useful in a situation where a user has increased vehicle speed above the current set-speed, for example by depressing the accelerator pedal 161, and after releasing the pedal 161 requires the vehicle 100 to slow more quickly than it would otherwise decelerate due to (say) powertrain braking alone, such as via engine compression braking.

It is to be understood that the control system 12 may be operable to allow a value of set-speed employed when operating in the first mode (LSP DC mode) to be different from that employed when operating in the second mode (LSP FF mode). Thus, the set-speed employed may depend on the mode in which the control system 12 is operating.

It will be understood that the embodiments described above are given by way of example only and are not intended to limit the invention, the scope of which is defined in the appended claims.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A system for controlling the speed of a vehicle, the system being configured to operate the vehicle in accordance with a current value of vehicle set-speed, the system comprising a controller configured to receive and output electrical signals to and from components of the vehicle, the controller being operable:
   in response to user input to change the current value of vehicle set-speed from the current value to a value different from the current value via a user interface;
   in response to the user input to store the current value of set-speed in a memory as a stored set-speed and to change the current value of set-speed in dependence on the user input; and
   to set the current value of vehicle set-speed to the stored set-speed in response to receipt of a user command.

2. A system according to claim 1, wherein the controller is operable to allow a user to change the current value of set-speed in discrete amounts via the user interface.

3. A system according to claim 1, wherein the controller is operable to provide a visual indication of the current value of set-speed and a visual indication of the value of stored set-speed.

4. A system according to claim 3, wherein the controller is operable to provide the visual indication in the form of a current set-speed marker or chaplet and a stored set-speed marker or chaplet at respective locations of a speedometer corresponding to the values of current and stored set-speed.

5. A system according to claim 3, wherein the controller is operable to set the current value of vehicle set-speed to the stored set-speed in response to receipt of the user command only if the user command is received within a prescribed time period of the change of set-speed.

6. A system according to claim 5, wherein the controller is operable to provide the visual indication of the stored set-speed only for the duration of the prescribed time period.

7. A system according to claim 1, wherein the controller is operable to set the current value of vehicle set-speed to the stored set-speed in response to receipt of the user command only if the user command is received within a prescribed time period of the change of set-speed.

8. A system according to claim 1, wherein the controller is operable to allow a user to command a reduction in the current value of vehicle set-speed by either one of first and second input devices, the controller being operable to store the current value of set-speed in a memory as the stored set-speed and subsequently to set the current value of vehicle set-speed to the stored set-speed in response to receipt of the user command only if the reduction in set-speed is commanded by the second input device.

9. A system according to claim 8 wherein the second input device is a user operable brake control.

10. A system according to claim 8 wherein the first input device is a user operable control button.

11. A vehicle comprising a system according to claim 1.

12. A method of controlling the speed of a vehicle, comprising:
operating a vehicle in accordance with a current value of vehicle set-speed;
receiving a user input to change the current value of vehicle set-speed from the current value to a value different from the current value via a user interface; and
in response to receipt of the user input to change the value of set-speed, storing the current value of set-speed in a memory as a stored set-speed and changing the current value of set-speed in dependence on the user input;
the method further comprising setting the current value of vehicle set-speed to the stored set-speed in response to receipt of a user command.

13. A method as set forth in claim 12 further comprising the steps of:
providing a visual indication of the current value of the set-speed in the form of a current set-speed marker or chaplet at a location on a speedometer corresponding to the current value of the set-speed; and
providing a visual indication of the value of the stored set-speed in the form of a stored set-speed marker or chaplet at a location on the speedometer corresponding to the value of the stored set-speed.

14. A method as set forth in claim 12 set the current value of vehicle set-speed to the stored set-speed in response to receipt of the user command only if the user command is received within a prescribed time period of the change of set-speed.

15. A method as set forth in claim 14 operable to provide the visual indication of the stored set-speed only for the duration of the prescribed time period.

16. A system for controlling the speed of a vehicle, the system being configured to operate the vehicle in accordance with a value of vehicle set-speed, wherein the system comprises a controller configured to receive and output electrical signals from and to one or more components of the vehicle, wherein:
in a first mode of operation of the system, the controller is operable to apply brake torque to one or more vehicle wheels in order to cause the vehicle to operate in accordance with a value of vehicle set-speed for the first mode and not to apply drive torque, and
in a second mode of operation of the system, the controller is operable to apply brake torque or drive torque to one or more vehicle wheels in order to cause the vehicle to operate in accordance with a value of vehicle set-speed for the second mode.

17. A system according to claim 16 wherein in the first mode the controller is operable to apply brake torque in order to cause the vehicle to operate in accordance with the value of first mode set-speed only when the controller determines that the vehicle is descending a slope.

18. A system according to claim 16, wherein the controller is operable to enter the first mode when system operation is requested, and when in the first mode the controller being operable to enter the second mode in response to a user command to enter the second mode input via the user interface.

19. A system according to claim 16, wherein the controller is operable to enter the first mode when system operation is requested provided a speed of the vehicle is below a first mode threshold value.

20. A system according to claim 19 wherein if the speed of the vehicle is not below the first mode threshold value when system operation is requested, the system is configured to enter a third mode corresponding to a standby mode in which the system is not operable to apply brake torque or drive torque to the one or more vehicle wheels.

* * * * *